United States Patent
Straub et al.

(10) Patent No.: US 9,545,599 B2
(45) Date of Patent: Jan. 17, 2017

(54) HYBRID MEMBRANE SYSTEM FOR GAS STREAMS WITH CONDENSABLE HYDROCARBONS

(71) Applicant: Generon IGS, Inc., Houston, TX (US)

(72) Inventors: Marc Straub, Brentwood, CA (US); John A. Jensvold, Benicia, CA (US)

(73) Assignee: Generon IGS, Inc., Houson, TX (US)

( * ) Notice: Subject to any disclaimer, the term of this patent is extended or adjusted under 35 U.S.C. 154(b) by 301 days.

(21) Appl. No.: 14/155,528

(22) Filed: Jan. 15, 2014

(65) Prior Publication Data

US 2014/0243572 A1 Aug. 28, 2014

Related U.S. Application Data

(60) Provisional application No. 61/770,387, filed on Feb. 28, 2013.

(51) Int. Cl.
*B01D 53/22* (2006.01)
*B01D 71/16* (2006.01)
*C07C 7/144* (2006.01)
*B01D 53/26* (2006.01)
(Continued)

(52) U.S. Cl.
CPC ............ *B01D 53/226* (2013.01); *B01D 53/22* (2013.01); *B01D 53/228* (2013.01); *B01D 53/268* (2013.01); *B01D 63/04* (2013.01); *B01D 71/16* (2013.01); *C07C 7/144* (2013.01); *C10L 3/101* (2013.01); *B01D 2256/245* (2013.01); *B01D 2257/504* (2013.01); *B01D 2257/702* (2013.01); *B01D 2313/12* (2013.01); *B01D 2319/022* (2013.01); *B01D 2319/06* (2013.01); *C10L 2290/548* (2013.01); *Y02C 10/10* (2013.01); *Y02P 20/152* (2015.11)

(58) Field of Classification Search
CPC ..... B01D 53/22; B01D 53/226; B01D 53/228; B01D 53/268; B01D 63/04; B01D 2256/245; B01D 2257/507; B01D 2317/02; B01D 2317/022; B01D 2317/08; B01D 2319/02; B01D 2319/022; B01D 2319/06; B01D 71/10; B01D 71/12; B01D 71/16; B01D 2319/064; C10C 7/144; C10L 3/101
USPC .............................................. 95/50, 51; 96/9
See application file for complete search history.

(56) References Cited

U.S. PATENT DOCUMENTS

| | | | | |
|---|---|---|---|---|
| 4,435,191 | A | * | 3/1984 | Graham ............... B01D 53/226 95/51 |
| 4,497,640 | A | * | 2/1985 | Fournie .................. B01D 53/22 95/10 |
| 4,553,983 | A | | 11/1985 | Baker |

(Continued)

*Primary Examiner* — Jason M Greene
(74) *Attorney, Agent, or Firm* — William H. Eilberg

(57) ABSTRACT

A gaseous component is extracted non-cryogenically from a feed gas containing condensable hydrocarbons. The feed gas is passed first through a module containing polymeric fibers useful for removing water vapor from the gas. The gas is then passed through a module containing polymeric fibers selected such that they remove some, but not all, of the carbon dioxide in the stream. The gas is then passed through a module containing polymeric fibers selected to remove at least some of the remaining carbon dioxide as well as heavy hydrocarbons, defined as C5 and heavier, from the stream. The invention is especially useful in processing raw methane taken from a well, and in producing methane which is relatively free of water vapor, carbon dioxide, and heavy hydrocarbons.

18 Claims, 2 Drawing Sheets

(51) Int. Cl.
*C10L 3/10* (2006.01)
*B01D 63/04* (2006.01)

(56) References Cited

U.S. PATENT DOCUMENTS

| | | | | |
|---|---|---|---|---|
| 4,676,808 A * | 6/1987 | Coplan | ............... | B01D 53/22 |
| | | | | 96/8 |
| 4,881,953 A | 11/1989 | Prasad | | |
| 5,176,725 A * | 1/1993 | Puri | ............... | B01D 53/22 |
| | | | | 96/8 |
| 5,332,498 A * | 7/1994 | Rogut | ............... | B01D 63/04 |
| | | | | 96/8 |
| 5,482,539 A * | 1/1996 | Callahan | ............ | B01D 53/226 |
| | | | | 95/45 |
| 5,772,734 A | 6/1998 | Baker | | |
| 6,053,965 A * | 4/2000 | Lokhandwala | ...... | B01D 53/229 |
| | | | | 95/49 |
| 6,153,097 A * | 11/2000 | Jensvold | ............ | B01D 63/026 |
| | | | | 96/10 |
| 6,352,575 B1 | 3/2002 | Lindsay | | |
| 7,294,174 B2 | 11/2007 | Coan | | |
| 7,497,894 B2 | 3/2009 | Jeffers | | |
| 7,517,388 B2 | 4/2009 | Jensvold | | |
| 7,578,871 B2 | 8/2009 | Jensvold | | |
| 7,662,333 B2 | 2/2010 | Coan | | |
| 2002/0152889 A1 * | 10/2002 | Baker | ............... | B01D 53/228 |
| | | | | 95/45 |
| 2011/0041687 A1 * | 2/2011 | Diaz | ............... | B01D 53/228 |
| | | | | 95/51 |
| 2011/0239866 A1 * | 10/2011 | Coan | ............... | B01D 53/228 |
| | | | | 96/9 |

* cited by examiner

HYBRID MEMBRANE SYSTEM FOR GAS STREAMS WITH CONDENSABLE HYDROCARBONS

CROSS-REFERENCE TO PRIOR APPLICATION

Priority is claimed from U.S. provisional patent application Ser. No. 61/770,387, filed Feb. 28, 2013, the disclosure of which is incorporated by reference herein.

BACKGROUND OF THE INVENTION

The present invention relates to the non-cryogenic separation of gas mixtures. The invention provides an improved method and system for separating a feed gas into components. The invention is especially suited to separation of a feed gas which contains condensable hydrocarbons.

It has been known to use a polymeric membrane to separate air into components. Various polymers have the property that they allow different gases to flow through, or permeate, the membrane, at different rates. A polymer used in air separation, for example, will pass oxygen and nitrogen at different rates. The gas that preferentially flows through the membrane wall is called the "permeate" gas, and the gas that tends not to flow through the membrane is called the "non-permeate" or "retentate" gas. The selectivity of the membrane is a measure of the degree to which the membrane allows one component, but not the other, to pass through.

A membrane-based gas separation system has the inherent advantage that the system does not require the transportation, storage, and handling of cryogenic liquids. Also, a membrane system requires relatively little energy. The membrane itself has no moving parts; the only moving part in the overall membrane system is usually the compressor which provides the gas to be fed to the membrane.

A gas separation membrane unit is typically provided in the form of a module containing a large number of small, hollow fibers made of the selected polymeric membrane material. The module is generally cylindrical, and terminates in a pair of tubesheets which anchor the hollow fibers. The tubesheets are impervious to gas. The fibers are mounted so as to extend through the tubesheets, so that gas flowing through the interior of the fibers (known in the art as the bore side) can effectively bypass the tubesheets. But gas flowing in the region external to the fibers (known as the shell side) cannot pass through the tubesheets.

In operation, a gas is introduced into a membrane module, the gas being directed to flow through the bore side of the fibers. One component of the gas permeates through the fiber walls, and emerges on the shell side of the fibers, while the other, non-permeate, component tends to flow straight through the bores of the fibers. The non-permeate component comprises a product stream that emerges from the bore sides of the fibers at the outlet end of the module.

Alternatively, the gas can be introduced from the shell side of the module. In this case, the permeate is withdrawn from the bore side, and the non-permeate is taken from the shell side.

An example of a membrane-based air separation system is given in U.S. Pat. No. 4,881,953, the disclosure of which is incorporated by reference herein.

Other examples of fiber membrane modules are given in U.S. Pat. Nos. 7,497,894, 7,517,388, 7,578,871, and 7,662,333, the disclosures of which are all hereby incorporated by reference.

Most gas streams, whether they originate from wells in the field, or whether they are taken from industrial processes, contain various impurities which must be removed, or minimized, if the gas stream is to be commercially useful. Typically, such impurities include water vapor, particulates, condensable hydrocarbon gases, and other less desirable gases.

Water vapor is usually removed with a vapor trap, while condensable hydrocarbon gases are removed by a carbon bed filter. Less desirable gases are often removed through the use of a selective membrane, or other gas separation method such as pressure swing adsorption or a cryogenic process.

Many polymer membranes become degraded in the presence of liquid water or water vapor. In such cases, the air directed into the membrane must be substantially free of water. For this reason, it is common to provide some form of dehydration unit which treats the gas before it flows through the membrane. Polymers have been developed which separate water vapor from a gas. An example of such a polymer is given in U.S. Pat. No. 7,294,174, the disclosure of which is incorporated by reference herein.

A polymer membrane may also be degraded by oil particulates and oil vapor, which may leak from the compressor.

In addition to a dehydration module and a carbon bed, one may provide heaters, moisture traps, and/or filters between the compressor and the membrane unit, as needed.

Some membranes are degraded by the presence of condensable hydrocarbons, especially those of high molecular weight. Such hydrocarbons, if present in a feed stream, may condense in the membrane, and will thus reduce the processing rate with regard to the incondensable components. The condensation thus reduces the overall efficiency of the gas separation process. If such condensable hydrocarbons are removed from the feed stream, the useful life and stability of the membrane can be readily increased.

Systems of the prior art have addressed the problems caused by the presence of volatile higher hydrocarbons by using process stream chillers and/or carbon beds, positioned upstream of the gas separation unit. A chiller causes the hydrocarbon to condense, so that the hydrocarbon can be conveniently removed as a liquid, before the feed gas flows into the membrane module.

The temperature to which the gas may be chilled is effectively limited, however, because it is necessary to avoid freezing the components of the feed gas, such as hydrocarbons, water vapor, and/or hydrates which could cause plugging of the process lines. Thus, chillers are of limited utility in reducing the concentration of hydrocarbons in the gas.

Carbon beds are useful in pre-treating a gas mixture, but such beds can quickly become filled with hydrocarbons, and the beds are difficult to regenerate. Such regeneration typically requires extremely high temperatures, and the regeneration process may take considerable time, further reducing the efficiency of the process.

Other examples of prior art devices for removal of hydrocarbons from gas streams are shown in U.S. Pat. Nos. 4,553,983, 5,772,734, and 6,352,575.

One application in which the present invention is especially useful, is the production of natural gas (methane). The gas taken from the well typically includes water vapor, carbon dioxide, and some heavier hydrocarbons, in addition to the methane. The object is to remove everything but the methane, or to produce a gas which is mainly methane with some additional hydrocarbons. However, no single membrane will work well under these conditions. A membrane which may work well in removing carbon dioxide or water may degrade quickly in the presence of condensable hydrocarbons.

The present invention solves the problem caused by differences in the properties of different membrane materials. The invention provides a commercially workable system and method for membrane-based separation of a gas, making possible the efficient removal of various impurities. The invention is not limited to use in the example given above, but can be used in other gas-separation applications.

SUMMARY OF THE INVENTION

The present invention comprises a multi-stage membrane system for gas separation. Each stage is tailored for a specific sub-task, such that the efficiency of the overall gas-separation process is enhanced.

In one example, the feed gas comprises the output stream of a natural gas well. The feed gas stream therefore includes primarily methane, but also includes water vapor, carbon dioxide, and various hydrocarbons.

For this example, the first stage of the membrane system of the present invention comprises a dehydration membrane module, which removes most of the water vapor. The second stage comprises a membrane module which removes some, but not all, of the carbon dioxide in the gas stream. The third stage comprises a membrane module which removes most of the remainder of the carbon dioxide. The third stage membrane is selected such that it is tolerant of liquid hydrocarbons, such that when the heavier hydrocarbons in the stream condense, the membrane will not be degraded.

By tailoring each membrane to a specific intended input and output, one can improve the performance of each sub-task of the process, and thereby improve the overall gas-separation process.

In the arrangement described above, the membrane modules are separate units arranged in series. In an alternative embodiment, all three stages are provided in a single unit. In this alternative, each membrane module is provided in the form of a woven mat made of polymeric fibers having a desired composition. These mats are concentric with a central core. Thus, the mats have a generally annular cross-section.

A feed gas is introduced on the shell side (the outside of the unit), passing first through the fibers of the outermost mat, then passing through the fibers of the next mat immediately inside the outer mat, and then passing through the fibers of the innermost mat. Thus, in this alternative arrangement, the feed gas still effectively passes through three separate membrane "modules", although these modules are contained within the same housing.

In another variation of the single-unit alternative, the unit can be configured such that the feed gas enters at the core, and passes radially outward, to be withdrawn at the shell side of the unit.

The present invention therefore has the primary object of improving the efficiency of gas separation using polymeric membranes.

The invention has the further object of providing a gas-separation method and apparatus which uses multiple stages, wherein each stage is optimized for efficiency for its particular sub-task.

The invention has the further object of providing a gas-separation method and apparatus which is especially useful in handling gas streams containing condensable hydrocarbons.

The invention has the further object of providing a membrane-based gas-separation system which overcomes the problem caused by membrane degradation due to condensation of water and/or hydrocarbons.

The reader skilled in the art will recognize other objects and advantages of the present invention, from a reading of the following brief description of the drawings, the detailed description of the invention, and the appended claims.

DETAILED DESCRIPTION OF THE INVENTION

The essence of the present invention is the provision of a series of gas-separation membrane modules which are tailored and arranged so as to remove different components of a feed gas stream, in an efficient manner, and in a continuous fashion.

In particular, each membrane module in the series is chosen according to the specific composition of the feed gas for that module, and what is expected to comprise the product gas of that module. In the present invention, no single membrane module is used to do every task. Instead, the gas-separation process is broken into smaller steps, each performed by a different membrane module which is best suited to the immediate sub-task.

Figure 1:
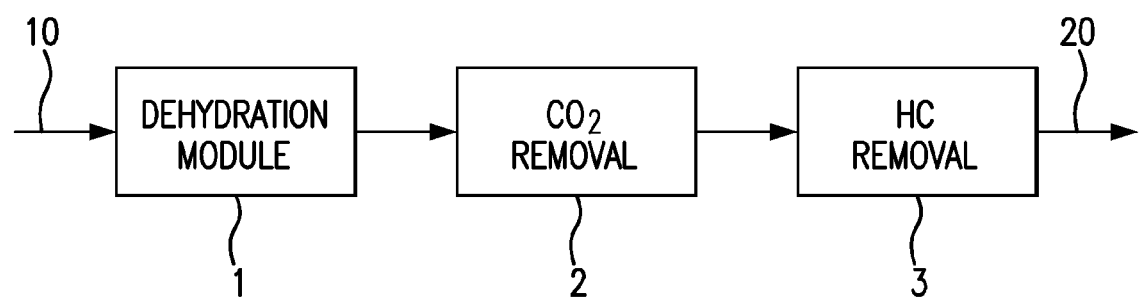
FIG. 1 provides a block diagram of a system of the present invention.

FIG. 1 illustrates a first embodiment of the present invention. A feed gas enters at conduit 10, and is conveyed into dehydration module 1. The dehydration module comprises a membrane for removing water vapor, but has little or no effectiveness in removing the component gases or contaminants. The dehydration module comprises hollow polymeric fibers, preferably polymers prepared by poly-condensation polymerization such as polycarbonate, polyester, polyether, polyimide, or polyamide, or, most preferably, polyether fibers such as polysulfone.

The product of module 1 is then directed into module 2, which comprises a membrane which removes some of the carbon dioxide, or carbon dioxide and water vapor, from the stream. The membrane in module 2 is chosen such that it will remove some, but not all, of the carbon dioxide in the stream. Removal of too much carbon dioxide, at this stage, would be disadvantageous, because it would increase the concentration of heavier hydrocarbons to the point that such hydrocarbons would condense and degrade the membrane. Such condensation would reduce the efficiency and/or durability of the membrane.

The material used for the membrane in module 2 may include polymeric hollow fibers, preferably polymers prepared by poly-condensation polymerization such as polycarbonate, polyester, polyether, polyimide, or polyamide, most preferably polyether fibers such as polycarbonate, even more preferably polycarbonate fiber prepared from tetrabromobisphenol A polycarbonate (TBBA). These membranes have a high permselectivity for carbon dioxide and water vapor over hydrocarbons, but a relatively low tolerance for condensing hydrocarbons.

The stream then passes into module 3, which will provide for the additional removal of carbon dioxide from light hydrocarbons (C1-C4) while tolerating and removing condensable hydrocarbons such as pentane, hexane, heptanes, octane, nonane, and decane, as well as C11-C20 hydrocarbons as they concentrate up in the feed gas to the point of saturation. This module can be called a C5+ module. It will remove the condensable higher hydrocarbons while concentrating the C1-C4 hydrocarbons through the continued removal of carbon dioxide.

The C5+ module comprises polymeric hollow fibers, with the fiber being chosen from cellulosic polymers, the most preferable fiber comprising cellulose triacetate fibers (CTA). While this type of membrane does not have as high a permselectivity for carbon dioxide over hydrocarbons as the previous module, it can tolerate and drain off condensed hydrocarbons from the feed stream.

The product of module 3 is directed through conduit 20. In the example wherein the feed gas is natural gas from a well, this product gas comprises mainly methane, and the product gas is relatively free of water vapor, carbon dioxide, and heavy hydrocarbons.

Each module can be fed from either the bore side or the shell side. Each module can be placed in a sequential position such that it will provide the greatest efficiency for the process. Water vapor may be more desirably removed first, while the condensable hydrocarbons may be removed next, and the gas separation process would be the last operation.

In summary, the present invention is based on the fact that a single membrane will have advantages and disadvantages with respect to each of the different gases passing through it. For example, a membrane which is very good at selecting for carbon dioxide is also likely to be degraded by condensation of heavy hydrocarbons. Thus, the invention comprises breaking the gas-separation process into "bite sized" pieces, and to require each module to do only that to which it is best suited.

Thus, in the example described herein, the first stage removes mainly water vapor, but not carbon dioxide or heavier hydrocarbons. The second stage has good selectivity for carbon dioxide (sometimes called the "fast" gas), so its job is to remove some (but not all) carbon dioxide while allowing other hydrocarbons to pass through. The third stage removes most of the remaining carbon dioxide, using a membrane which does not degrade when some of the heavier hydrocarbons liquefy. But the selectivity of the third stage for carbon dioxide is not as good as that of the second stage membrane. But by the time the gas stream has reached the third stage, much of the carbon dioxide has already been removed.

Figure 2:
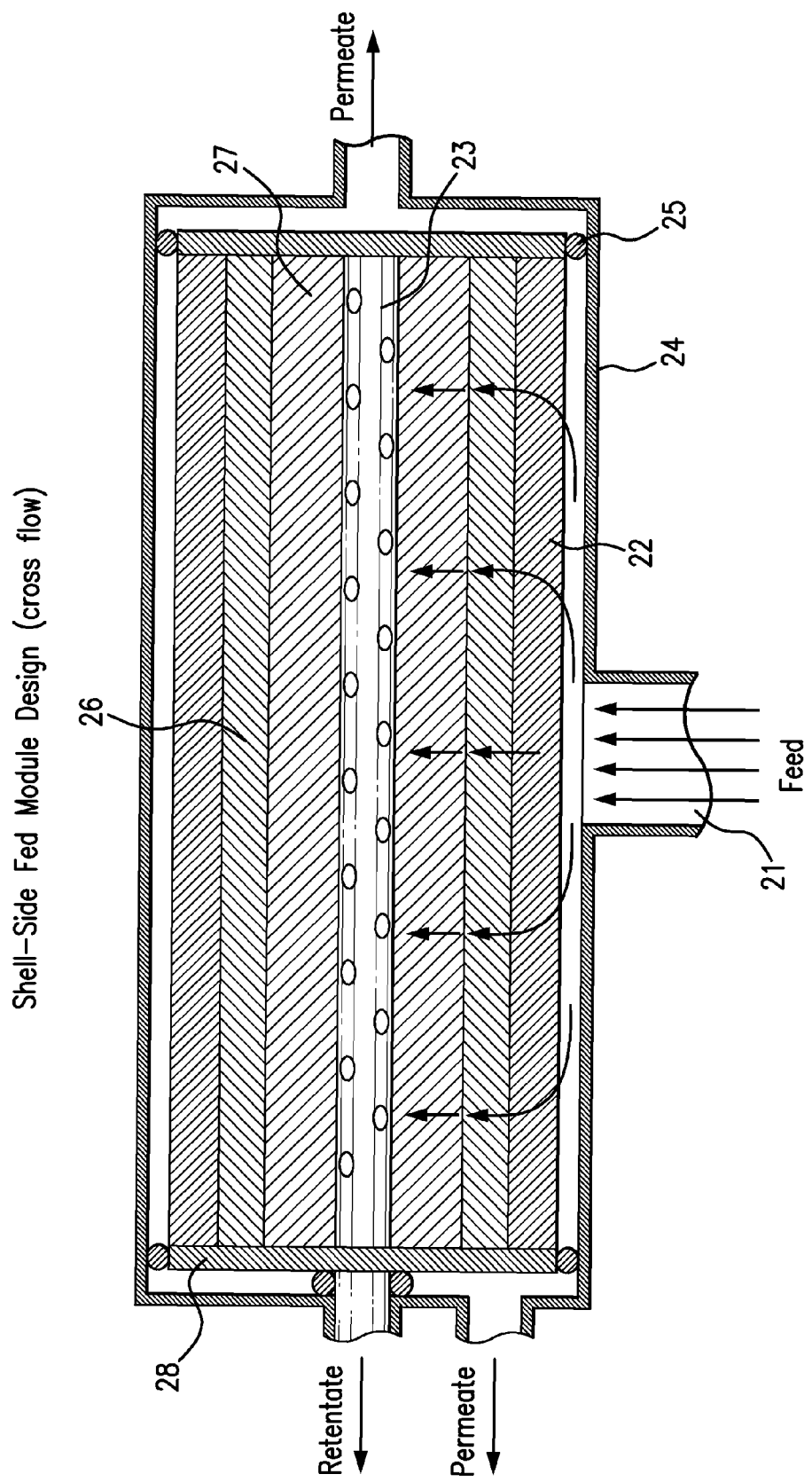
FIG. 2 provides a cross-sectional view of another embodiment of the present invention, showing a single unit which effectively includes three separate membrane modules.

In an alternative embodiment, the same process can be practiced with a single unit which effectively combines the functions of the three modules of FIG. 1 in one housing. FIG. 2 shows this alternative arrangement.

In FIG. 2, each type of polymeric fiber is woven into a mat, and the mats of fibers are arranged around a core tube in the most preferential order. In effect, each mat comprises the fibers of a different membrane module, and the three modules are arranged concentrically. Thus, the modules each have a generally annular cross-section. In the preferred embodiment, the feed gas can enter from the shell side, and the product can be extracted from the core tube. However, the same arrangement could be configured to operate with a bore-side feed.

FIG. 2 represents the case of shell-side feed. In FIG. 2, the various types of fiber are illustrated symbolically, through the use of different cross-hatchings. In reality, the fibers are tiny, and not readily illustrated.

In the embodiment of FIG. 2, the feed gas is directed through port 21, into dehydration fiber 22, which is arranged concentrically around core tube 23. The feed gas is at a relatively high pressure, and it therefore quickly becomes distributed along the entire length of the fiber. Water vapor preferentially passes into the bore of the fiber, and escapes at either end of the fiber as permeate. The remaining components of the feed gas, such as carbon dioxide and other hydrocarbons, comprise the retentate stream, which is held within the outer casing 24 by O-rings 25. Tubesheet 28 separates the high and low pressure areas of the hollow fiber membranes.

Next, the retentate gas (the product stream of the dehydration module) passes to the second stage, which comprises permselective fiber 26, which is immediately adjacent to the dehydration fiber, and closer to the core tube 23. The permselective fiber is the fiber having high selectivity for carbon dioxide (the fast gas) and light hydrocarbons. The carbon dioxide preferentially permeates the fiber, and is removed as waste. The product stream of the second stage is the retentate gas.

The retentate gas of the second stage then passes into the third stage, which is hydrocarbon fiber 27, located closest to the central core. Fiber 27 is the fiber which is tolerant of condensable hydrocarbons having molecular weight of C5 and above. For this third stage, the permeate includes some carbon dioxide and some hydrocarbons. The retentate will include some liquid in the gas stream, but, as explained above, this liquid will not degrade the membrane of this stage. The retentate is withdrawn as the final product stream.

In FIG. 2, the ports labeled "permeate" are connected to all of the modules, so that the permeate gases from each stage are ducted into the same channel. It is the retentate gas, which has not permeated any of the fibers of any of the modules, that is extracted as the final product gas.

Although the invention has been described with respect to a specific composition of feed gas, it should be understood that the invention can be applied to other feed gases having different compositions. In general, the choice of materials for the membranes may be different for different compositions of feed gas. The essence of the present invention is that it provides separate modules, tailored for specific feed and product gases, wherein each module is thereby optimized for its specific sub-task.

The invention can therefore be modified in ways that will be apparent to those skilled in the art. Such modifications should be deemed within the spirit and scope of the following claims.

What is claimed is:

1. Apparatus for extracting a gaseous component from a gas stream containing condensable hydrocarbons, the apparatus comprising three distinct modules connected in series, each module comprising a plurality of hollow polymeric fibers, wherein a first module comprises fibers made of a polymeric membrane which is useful for removal of water vapor from a gas stream, and which is of lesser effectiveness in removing components other than water vapor, wherein a second module comprises fibers made of a polymeric membrane selected such that it removes some, but not all, of carbon dioxide in a gas stream, and wherein a third module comprises fibers made of a polymeric membrane selected such that it removes carbon dioxide and removes heavy hydrocarbons, defined as C5 and heavier, from a gas stream, wherein the polymeric membrane of the third module has a selectivity for carbon dioxide which is less than a selectivity for carbon dioxide of the polymeric membrane of the second module.

2. The apparatus of claim 1, wherein the fibers of the first module are made of a material selected from the group consisting of polycarbonate, polyester, polyether, polyimide, polyamide, and polysulfone.

3. The apparatus of claim 1, wherein the fibers of the second module are made of a material selected from the group consisting of polycarbonate, polyester, polyether, polyimide, polyamide, and polycarbonate fiber prepared from tetrabromobisphenol A polycarbonate (TBBA).

4. The apparatus of claim 2, wherein the fibers of the second module are made of a material selected from the group consisting of polycarbonate, polyester, polyether, polyimide, polyamide, and polycarbonate fiber prepared from tetrabromobisphenol A polycarbonate (TBBA).

5. The apparatus of claim 1, wherein the fibers of the third module are made of a material selected from the group consisting of cellulosic polymers and cellulose triacetate (CTA).

6. The apparatus of claim 2, wherein the fibers of the third module are made of a material selected from the group consisting of cellulosic polymers and cellulose triacetate (CTA).

7. The apparatus of claim 3, wherein the fibers of the third module are made of a material selected from the group consisting of cellulosic polymers and cellulose triacetate (CTA).

8. The apparatus of claim 4, wherein the fibers of the third module are made of a material selected from the group consisting of cellulosic polymers and cellulose triacetate (CTA).

9. The apparatus of claim 1, wherein the modules comprise mats of fibers which are arranged concentrically around a core tube, and wherein the modules are enclosed within a common casing.

10. Apparatus for extracting a gaseous component from a gas stream containing condensable hydrocarbons, the apparatus comprising three distinct mats, each mat comprising a plurality of hollow polymeric fibers, each of the mats having a generally annular cross-section, the mats being arranged concentrically around a core tube, the mats being enclosed within a casing, the apparatus including an inlet port enabling a feed gas to be introduced into an outermost mat, at least one permeate outlet port for removing gas which has permeated through any one of said mats, and a retentate outlet port for removing gas which has not permeated through any of said mats, wherein a first of said mats comprises fibers made of a polymeric membrane which is useful for removal of water vapor from a gas stream, and which is of lesser effectiveness in removing components other than water vapor, wherein a second of said mats comprises fibers made of a polymeric membrane selected such that it removes some, but not all, of carbon dioxide in a gas stream, and wherein a third of said mats comprises fibers made of a polymeric membrane selected such that it removes carbon dioxide and removes heavy hydrocarbons, defined as C5 and heavier, from a gas stream, wherein the polymeric membrane of the third mat has a selectivity for carbon dioxide which is less than a selectivity for carbon dioxide of the polymeric membrane of the second mat.

11. The apparatus of claim 10, wherein said first mat comprises the outermost mat, wherein said second mat is positioned within the first mat, and wherein said third mat is positioned within the second mat and around the core tube.

12. A method for extracting a gaseous component from a gas stream containing condensable hydrocarbons, comprising the steps of:

passing a gas stream through a first module comprising fibers made of a polymeric membrane which removes water vapor from said gas stream, the first module producing an output stream, passing the output stream of the first module into a second module comprising fibers made of a polymeric membrane selected to remove some, but not all, of carbon dioxide in said stream, the second module producing an output stream, and passing the output stream of the second module into a third module comprising fibers made of a polymeric membrane selected to remove carbon dioxide and heavy hydrocarbons, defined as C5 and heavier, from the stream, wherein the method includes choosing the polymeric membrane of the third module to have a selectivity for carbon dioxide which is less than a selectivity for carbon dioxide of the polymeric membrane of the second module.

13. The method of claim 12, further comprising selecting the material for the polymeric membrane of the first module such that the material is useful for removal of water vapor from the stream, and which is of lesser effectiveness in removing components other than water vapor.

14. The method of claim 12, wherein the modules are connected in series, as distinct units.

15. The method of claim 12, wherein the first, second, and third modules each comprise a mat formed of polymeric fibers, the mats being arranged concentrically around a core tube, and contained in a common casing, and wherein the method includes introducing the gas stream into an outermost mat, wherein retentate gas from the outermost mat flows into a next inner mat, wherein retentate gas from the next inner mat flows into an innermost mat, and wherein retentate gas from the innermost mat comprises a product gas.

16. The method of claim 12, further comprising selecting the fibers of the first module to be made of a material selected from the group consisting of polycarbonate, polyester, polyether, polyimide, polyamide, and polysulfone.

17. The method of claim 12, further comprising selecting the fibers of the second module to be made of a material selected from the group consisting of polycarbonate, polyester, polyether, polyimide, polyamide, and polycarbonate fiber prepared from tetrabromobisphenol A polycarbonate (TBBA).

18. The method of claim 12, further comprising selecting the fibers of the third module to be made of a material selected from the group consisting of cellulosic polymers and cellulose triacetate (CTA).

* * * * *